(12) United States Patent
Van Der Borght et al.

(10) Patent No.: US 9,375,572 B2
(45) Date of Patent: \*Jun. 28, 2016

(54) HEARING PROSTHESIS SYSTEM HAVING INTERCHANGEABLE HOUSINGS

(71) Applicant: Cochlear Limited, Macquarie University, NSW (AU)

(72) Inventors: Gunther Van Der Borght, Artarmon (AU); Jan Janssen, St. Ives (AU)

(73) Assignee: Cochlear Limited, Macquarie University, NSW (AU)

( \* ) Notice: Subject to any disclaimer, the term of this patent is extended or adjusted under 35 U.S.C. 154(b) by 0 days.

This patent is subject to a terminal disclaimer.

(21) Appl. No.: 14/337,540

(22) Filed: Jul. 22, 2014

(65) Prior Publication Data

US 2015/0051667 A1     Feb. 19, 2015

Related U.S. Application Data

(63) Continuation of application No. 10/582,240, filed as application No. PCT/AU2004/001803 on Dec. 22, 2004, now Pat. No. 8,788,050.

(30) Foreign Application Priority Data

Dec. 22, 2003   (AU) ................................ 2003907101

(51) Int. Cl.
*A61N 1/00* (2006.01)
*A61N 1/36* (2006.01)
*H04R 25/00* (2006.01)
*A61N 1/372* (2006.01)

(52) U.S. Cl.
CPC ........ *A61N 1/36032* (2013.01); *A61N 1/37247* (2013.01); *H04R 25/43* (2013.01); *H04R 25/556* (2013.01); *H04R 25/65* (2013.01); *H04R 25/554* (2013.01); *H04R 25/558* (2013.01); *H04R 2225/67* (2013.01)

(58) Field of Classification Search
CPC ........... A61N 1/36032; A61N 1/37211; A61N 1/375; A61N 1/37247; H04R 25/43; H04R 25/556; H04R 25/65
See application file for complete search history.

(56) References Cited

U.S. PATENT DOCUMENTS 5,824,022 A \* 10/1998 Zilberman et al. .............. 607/57

\* cited by examiner

*Primary Examiner* — Scott Getzow
(74) *Attorney, Agent, or Firm* — Hauptman Ham, LLP

(57) ABSTRACT

There is disclosed a hearing prosthesis comprising a first housing containing a primary signal processor that receives signals output by a microphone; and a second housing removably connectable to the first housing; wherein a user interface is provided on the second housing that provides control of one or more features of the operation of the primary signal processor.

24 Claims, 5 Drawing Sheets

HEARING PROSTHESIS SYSTEM HAVING INTERCHANGEABLE HOUSINGS

CROSS-REFERENCE TO RELATED APPLICATIONS

The present application is continuation of U.S. patent application Ser. No. 10/582,240, filed on Aug. 4, 2008, now U.S. Pat. No. 8,788,050, issued on Jul. 22, 2014, which is a national stage of International Application No. PCT/AU2004/001803, filed on Dec. 22, 2004, which claims priority from AU Patent Application No. 2003907101, filed on Dec. 22, 2003. The contents of these applications are hereby incorporated by reference herein.

BACKGROUND

1. Field of the Invention

This present invention is generally directed to auditory prosthesis, and more particularly, to an external speech processor unit for an auditory prosthesis.

2. Related Art

A Cochlear™ implant hearing prosthesis (also referred to as a Cochlear™ prosthesis, and the like, collectively and generally referred to herein as "cochlear implant") delivers electrical stimulation to the auditory nerve fibres thereby allowing the brain to perceive a hearing sensation resembling the natural hearing sensation normally delivered by the auditory nerve.

As shown in prior art drawing FIG. 5, a cochlear implant hearing prosthesis typically comprises an external assembly of components 51 and an implantable assembly of components 52.

The external assembly 51 includes a primary signal processor unit in the form of a speech processor unit 56, a transmission coil 57 and a microphone unit 58. The primary signal processor unit includes an internal power source, such as a number of batteries, and is connected to each of the transmission coil 57 and microphone unit 58 via cables 59.

The internal assembly 52 typically includes a receiver antenna 55, a receiver/stimulator unit 53, and an intracochlear electrode assembly 54.

In operation, the microphone 58 detects sounds, such as speech and environmental sounds and converts these into an electrical signal. The electrical signal is then encoded by the speech processing electronics in the primary signal processor unit 56. The encoded output signal is transcutaneously transmitted to the internal assembly 52 via a radio frequency (RF) link.

In recent times, the speech processor unit and the microphone unit have been combined to form a single unit that is worn behind the ear. This is referred to as a behind the ear (BTE) speech processor unit.

Referring to prior art drawing FIG. 6, the BIB speech processor unit 61 is normally manufactured by mould a main body and an inter-engageable battery carrier. This arrangement enables the batteries 62 to be readily replaced.

The BTE speech processor unit 61 is relatively expensive and must undergo an optimisation procedure following implantation of the implantable assembly 52. While the operability of the signal processing aspects of the BTE speech processor unit can be varied by clinical software during the optimisation procedure, usually in a clincian's practice, other aspects of operability are far more limited. This is particularly the case with external user inter-actable features.

It is desired to provide an arrangement that improves upon earlier proposals, or at least provides a useful alternative.

SUMMARY

According to a first aspect, the present invention is a hearing prosthesis system comprising: a first housing containing a primary signal processing unit that receives signals output by a microphone; and a plurality of second housings that are removably connectable to the first housing; wherein only one of said second housings is connectable to said first housing at any one time and further wherein at least one of said second housings has a user interface that provides control of one or more features of the operation of the primary signal processor.

According to a second aspect the present invention is a hearing prosthesis comprising: a first housing containing a primary signal processor that receives signals output by a microphone; and a second housing removably connectable to the first housing, wherein a user interface is provided on the second housing that provides control of one or more features of the operation of the primary signal processor.

According to a third aspect, the present invention is a hearing prosthesis comprising: a first housing containing a primary signal processor that receives sirs output by a microphone; and a remote module; wherein a user interface is provided on the remote module that provides control of one or more features of the operation of the primary signal processor.

According to another aspect, the present invention is a speech processing unit for a hearing pros thesis rte speech processing unit comprising: a main part configured for wearing behind an ear of the hearing prosthesis recipient, the main part including a primary signal processor for carrying out primary signal processing functions associated with the speech processing unit; and a replaceable part being removably connectable with the pry part, the replaceable part including a user interface for communication with the primary signal processor.

According to another aspect, the present invention is a speech processing unit for a cochlear implant recipient, the speech processing unit comprising: a main part configured for wearing behind an ear of the cochlear implant recipient, the main part including a primary signal processor for out primary signal processing functions associated with the speech processing unit; and a replaceable part being removably connectable with the primary part, the replaceable part including a battery compartment and user interface for communication with the primary signal processor.

BRIEF DESCRIPTION OF THE DRAWINGS

Embodiments of the present invention are described below with reference to the attached drawings, in which.

DETAILED DESCRIPTION

Figure 1:
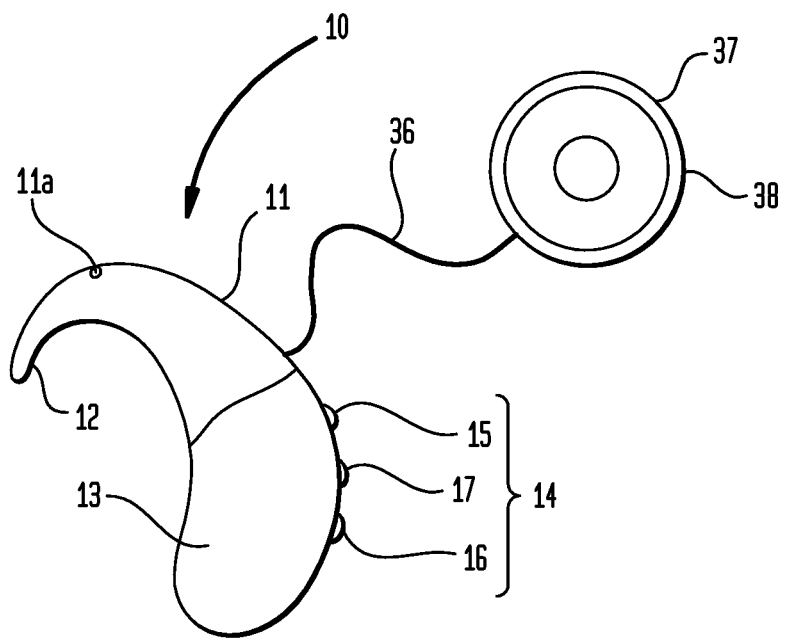
FIG. 1 is a side elevation view of an ex component of a hearing prosthesis according to the present disclosure.

Referring to FIG. 1, a BTE speech processor unit 10 includes a first housing 11 (or a main part), an ear hook 12 and a second housing 13 (or replaceable part). The first and/or second housing can be formed of a metallic material a ceramic material a polymeric material, or some combination thereof.

The BTE speech processor unit 10 is connected to a headpiece 37 via cable 36 which extends from the first housing 11.

The first housing 11 includes a signal processing electronics for operating the BTE speech processor unit 10. In this example, a microphone 11a is mounted on the first housing 11. However, the microphone can be positioned elsewhere, such as on the headpiece 37, on the second housing 13, or on the clothing of the recipient.

The headpiece 37 comprises an antenna coil 38 that is capable of transmitting signals to a complementary antenna implanted within the recipient in addition, the antenna coil 38 is capable of receiving signals transmitted from the implanted antenna. The antenna coil 38 surrounds a magnet 39 that is attracted to a complementary magnet implanted within the recipient. The magnetic attraction serves to retain the antenna coil 38, during use, in the desired position on the head of the recipient.

The speech processor unit 10 further comprises a second housing 13 that is removably connectable to the it housing 11. It is envisaged that the second housing 13 is normally replaceable by the recipient.

The second housing 13 includes a user interface panel 14 bang two push buttons 15, 16 and a dial 17. Push button 15 is used to activate and deactivate the speech processor within the first housing 11 and is also used to select the speech processor programme being performed by the speech processor. The dial 17 allows adjustment of the volume and sensitivity of the speech processor while the push button 16 allows the recipient or their carer to select whether the input to the speech processor is provided by the microphone, a telecoil or a mire of inputs. The user interface panel 14 is either removably or non-removably mounted to the second housing 13.

The present inventors have realised that providing for replaceability or interchangeability of the user interface can provide significant recipient benefits, compared with the manufacturing costs and total purchasing costs for an external component assembly of a hearing prosthesis. For example, it may be desired to provide larger push buttons for the elderly while children and infants may require more simplified interlockable controls. Similarly, an experienced user may require a more complex interface and/or greater flexibility with the internal workings of the speech processor.

Another advantage includes that the recipient can choose the user interface that suits them and/or their lifestyle. They also have the option of being able to delay a final decision as to which user interface they wish to use until after the purchase of the speech processor unit. If desired, they also have the option of changing the user interface of their system without the need to purchase a new speech processor unit.

The system also has advantage a the user is able to upgrade their user interface if and when desired. An upgrade may be made because a new type of user interface has been made available and/or because the user interface has failed and so needs to be replaced. The user interface being actuable is vulnerable to damage and this ability to be able to replace the user interface without having necessarily to replace the speech processor unit is an advantage of the present system.

A further advantage of the BTE speech processor unit is that the parts which are most vulnerable to damage and/or that are less expensive can be easily replaced.

Figure 2:
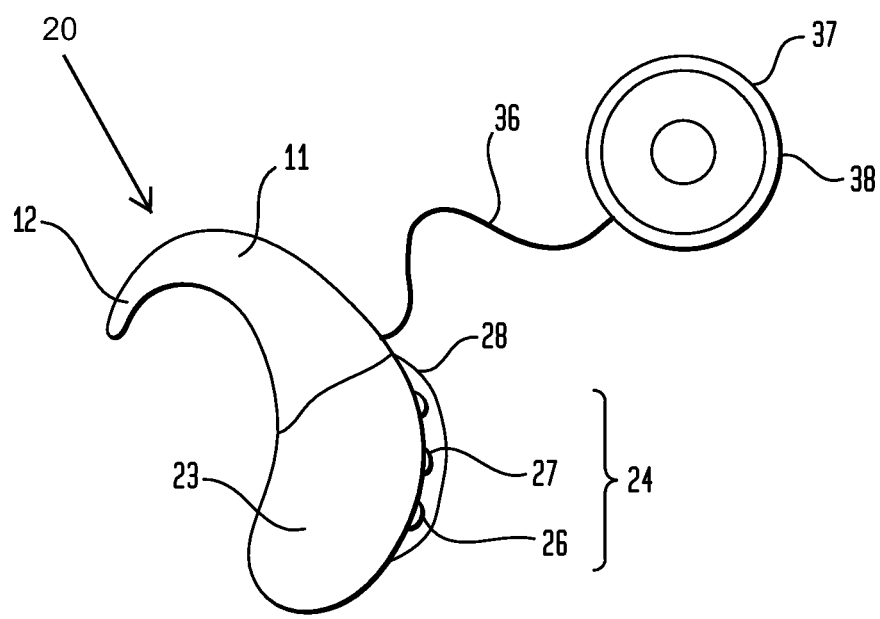
FIG. 2 is a side elevation view of another external component of a hearing prosthesis according to the present disclosure.

Turning now to FIG. 2, there is depicted a BTE speech processing unit 20 having an alternative user interface panel 24. As with the user interface panel described in relation to FIG. 1, the interface panel 24 of FIG. 2 can be removably or non-removably mounted to the second housing 23.

The user interface panel 24 includes two tactile position controls 25, 26 that, through their position provide feedback to the recipient and/or their carer as to the setting of that control. Both tactile position controls 25, 26 comprise a switch that is movable between at least three settings. Switch 25 is a three-position switch that allows a recipient and/or their carer to select which speech programme is to be used. Dial 27 allows adjustment of the volume and sensitivity of the speech processor. Switch 26 allows a recipient and/or their carer to set whether the speech processor is receiving input from the microphone, a telecoil, or a mix of such inputs. The switch 26 also allows the recipient and/or their carer to adjust the operation of the speech processor such that it cm detect relatively softer sounds, such as whisper.

In FIG. 2, the user interface 24 is enclosed within a resiliently flexible cover 28. The cover 28 protects the user interface 24 but also allows more precise control of the user interface 24 by the recipient and/or their carer.

In the arrangements shown in FIGS. 1 and 2, the first housing 11 for the speech processor is provided without a user interface. Therefore, any modification of its performance must be performed through the user interface on the second housing (13 or 23).

As shown in FIGS. 1 and 2, more than one type of second housing can be removably mountable to the first housing 11. The various types of second housing can vary in the type of user interface panel that is provided thereon. This allows a recipient and/or their carer to customise the hearing prosthesis by selecting the user interface to be used with their hearing prosthesis at any one time.

The first housing containing the speech processor unit can be connectable to more than one type of power supply. In the examples of FIGS. 1 and 2, the second housing (13 or 23) contains a power supply for powering the componentry of the prosthesis. On mounting of the second housing (13 or 23) to the first housing (11), the power supply is able to provide power through an electrical connection to the speech processor. Preferably, the power supply within the second housing comprises one or more rechargeable batteries.

Figure 3:
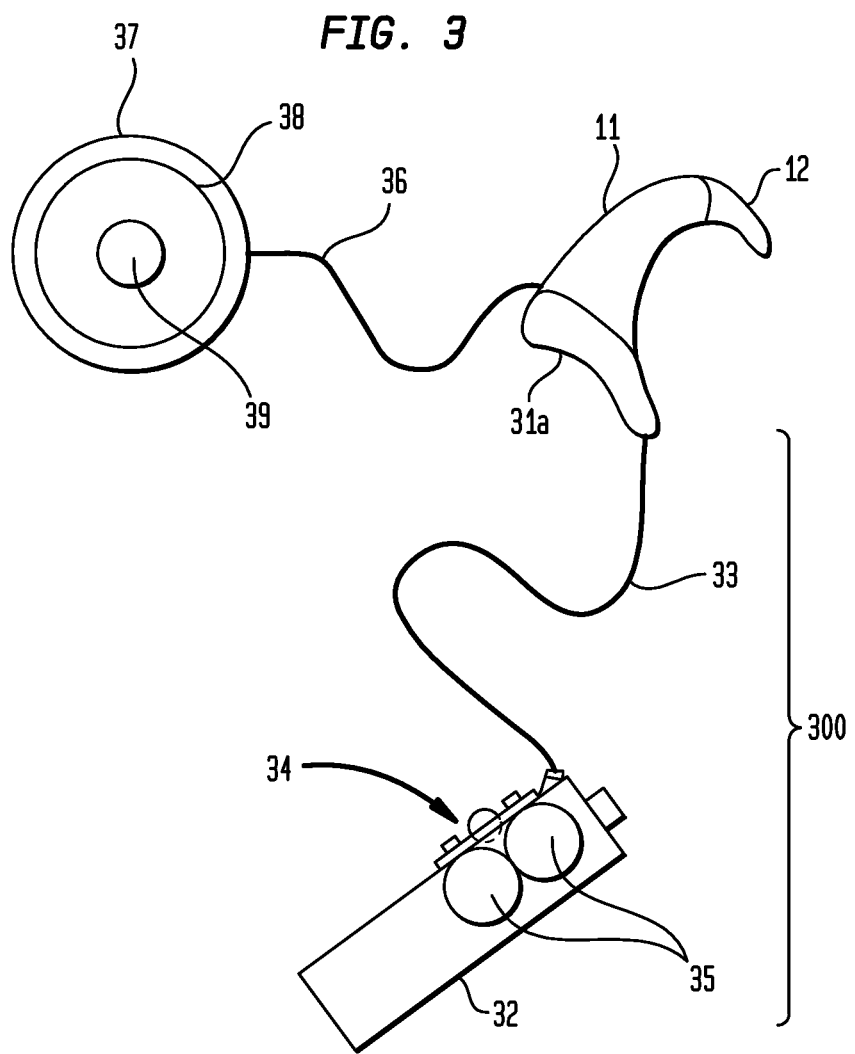
FIG. 3 is a view of another external component of a hearing prosthesis according to the present disclosure.

Referring now to FIG. 3, there is shown the fit housing 11 and an ear hook 12 as earlier described in relation to FIG. 1. However in comparison with the arrangement described in relation to FIG. 1, the second housing 13 is replaced by assembly 300. Assembly 300 includes a connector unit 31a and a remote module 32, connected via cable 33.

The first housing 11 relies on cable 33 to provide data and power transfer between the remote module 32 and a connector nit 31a that is removably connectable with the speech processor 31. However, it will be appreciated that wireless transmission can be utilised to transfer data and control signals between the remote module 32 and the speech processor and/or vice versa.

The remote module 32 includes a user interface panel 34, which is optionally removable/replaceable from the connector unit 31a. In the case of a removable replaceable interface panel 34, this allows a recipient and/or their carer to further customise the hearing prosthesis by selecting the user interface to be used with their hearing prosthesis at any one time.

The user interface panel 34 includes two push-button switches and a dial similar to that of user interface panel 14 earlier described in relation to FIG. 1.

In the example shown in FIG. 3, the remote module 32 also houses a power supply for at least some of the componentry of the external component 30 and particularly the speech processor. Preferably, the power supply comprises two rechargeable batteries 35.

The remote module 32 can be worn on the body of the recipient such as by being clipped to or placed in the pocket of clothing of the recipient.

Figure 4:
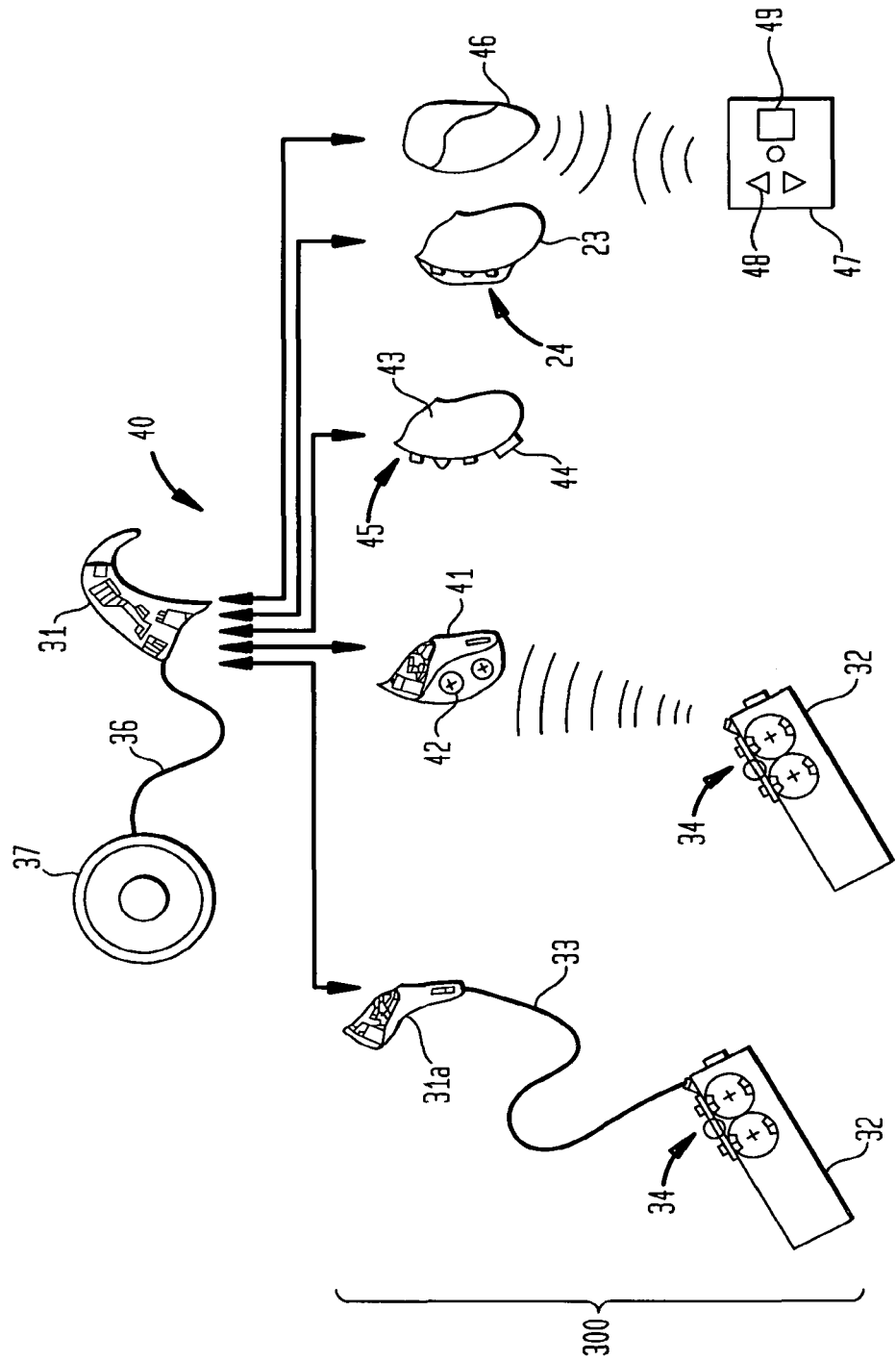
FIG. 4 is a schematic view of a hearing prosthesis system according to the present disclosure.
Figure 5:
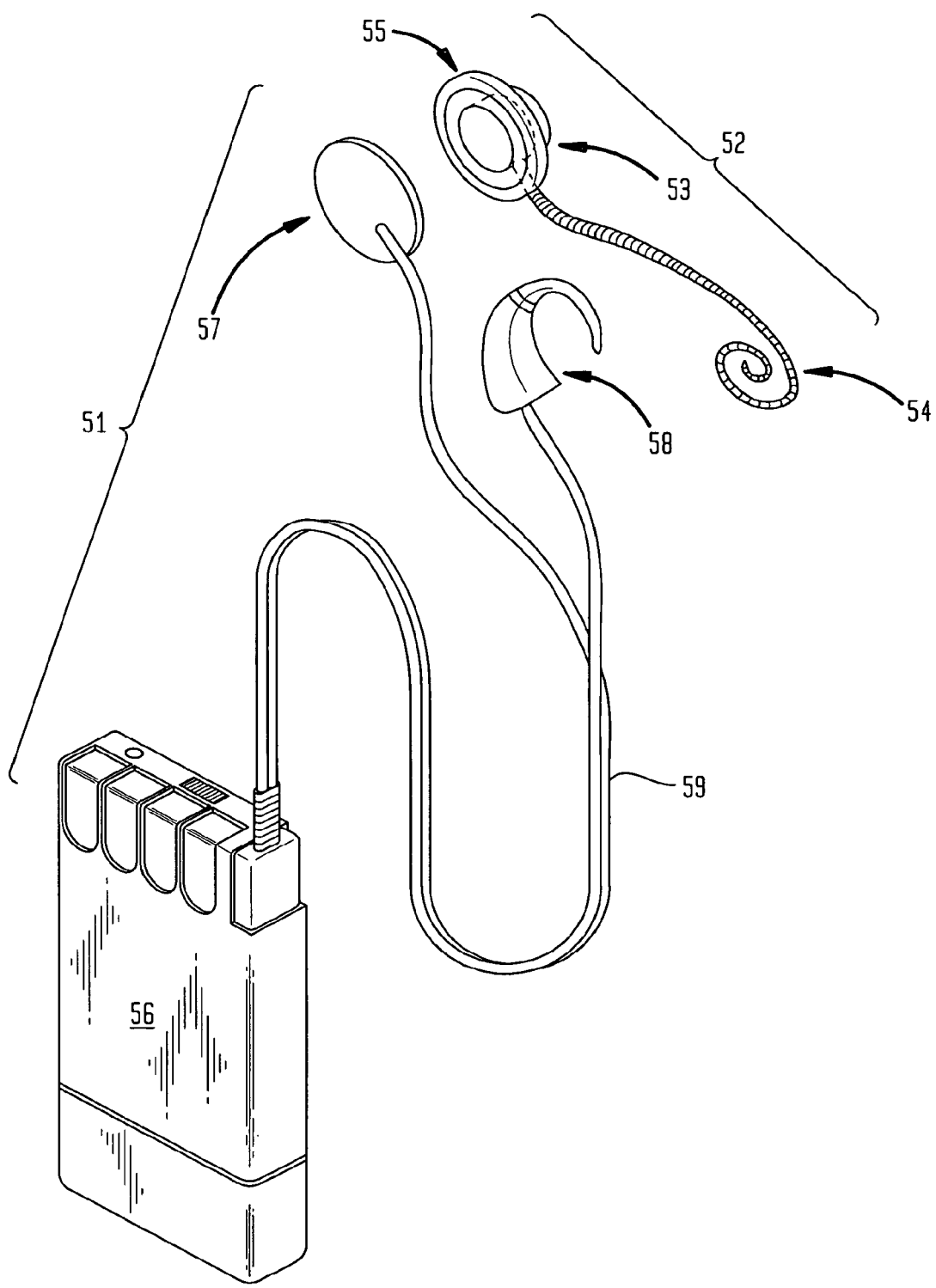
FIG. 5 is an example of a prior art extend assembly.
Figure 6:
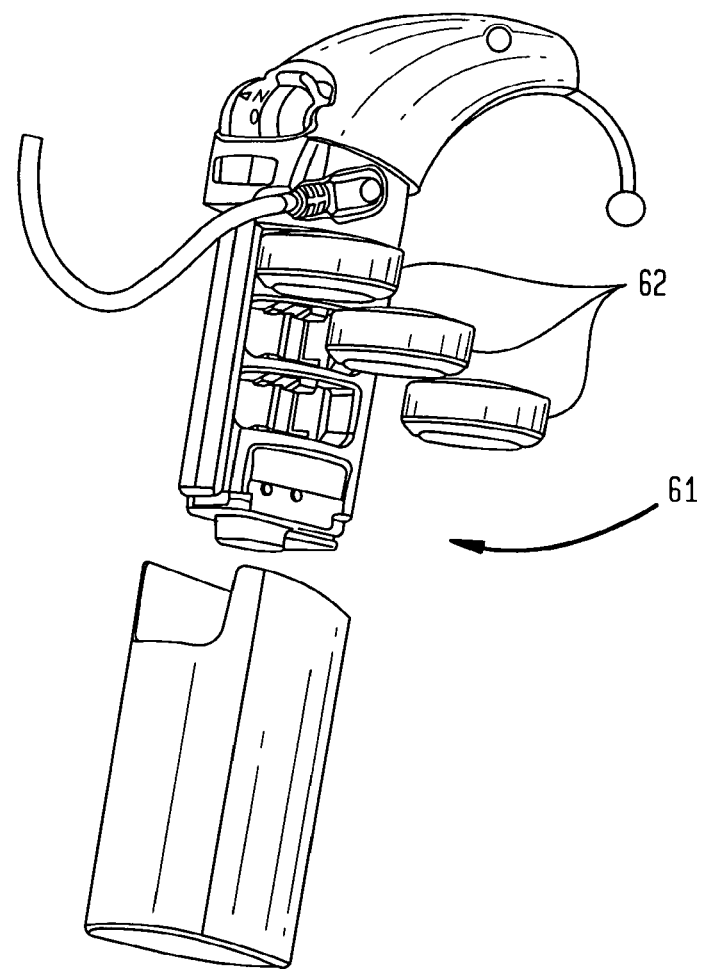
FIG. 6 is another example of a prior art external assembly.

A system of interchangeable parts will now be described with reference to FIG. 4.

The first housing 11 can be provided as part of a hearing prosthesis system 40 which can provide several interchangeable configurations. Hence the recipient or their carer is provided with a number of options as to what may be connected to the speech processor 31 housing at any one time.

The system 40 includes an option to connect a second housing 41 that includes a power supply 42 and radio frequency (RF) signal receiver circuitry that receives and processes RF signals output by the remote module 32. In this arrangement, the remote module 32 incorporates RF signal transmission circuitry for transiting signal to the housing 41 in response to adjustments made to the user interface 34 on the remote module 32.

The system 40 can also include an option to connect a second housing 43 that includes a power supply, a visual display device 44 and user interface 45. The exemplary display device 44 is a liquid crystal display, however, other suitable displays are envisaged. The liquid crystal display 44 provides feedback to the recipient or their carer as to the performance of the system 40.

The system 40 can also include an option to connect a second housing 46 that includes a power supply and circuitry that not only receives and processes RF signals but also can transmit signals back to a remote module 47. In this case, the remote module 47 as well as housing a power source has a user interface 48 and a liquid crystal display (LCD) 49 for providing feedback to the recipient or their carer as to the performance of the system 40.

Optionally, the first housing user interface can control some or all of the same features that are controllable by the user interface on the second housing 23 and/or the remote module 32. The first housing user interface, if present, can be rendered partially or fully inoperable when a second housing 23 and/or remote module 32 as defined herein is used in conjunction with the first housing of the hearing prosthesis. The first housing user interface can be removably or non-removably mounted to the first housing.

The user interface of the second housing 23 and/or the remote module 32 can be selected from a range of types of user interfaces that are available for use by the recipient of the hearing prosthesis or the recipients carer. For example, the user interface of the second hot 23 can be the same or different from available on a remote module 32. Where a user interface is provided on the first housing, the user interface of the second housing and/or the remote module can be different from that provided on the first housing.

In alternative configurations, one form of a user interface can be provided on the first housing 11 to control different features of the hearing prosthesis than that of the features controlled by the user interface panel of the second housing 23 and/or the remote module.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiment without departing from the spirit or scope of the invention as broadly described. The present embodiments are, therefore, to be considered in all respects as illustrative and not restrictive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A hearing prosthesis system comprising:
a first housing containing a primary signal processor, that receives signals output by a microphone; and
a plurality of second housings that are removably connectable to the first housing;
wherein only one of said second housings is connectable to said first housing at any one time and further wherein at least one of said second housings has a user interface that provides control of one or more features of the operation of the primary signal processor.

2. The hearing prosthesis of claim 1, wherein:
the first housing is configured such that when a respective second housing of the plurality of housings is removably connected to the first housing, a body of the first housing is in direct contact with a respective body of the respective second housing.

3. The hearing prosthesis of claim 1, wherein:
the first housing and the respective second housings are configured to be removably connected to one another such that at least one of (i) the first housing supports the respective second housings when removably connected to the first housing or (ii) visa-versa.

4. The hearing prosthesis of claim 1, wherein:
the first housing and the respective second housings are configured to be removably connected to one another such that when the first housing is removably connected to the respective second housings, the respective second housings is spatially fixed relative to the first housing in three axes of the Cartesian coordinate system relative to the first housing.

5. The hearing prosthesis of claim 1, wherein:
the first housing and the respective second housings are respectively configured such that the first housing and the respective second housings is respectively removably structurally supportably connected when connected.

6. A hearing prosthesis comprising:
a first housing containing a primary signal processor that receives signals output by a microphone; and
a second housing removably connectable to the first housing;
wherein a user interface is provided on the second housing that provides control of one or more features of the operation of the primary signal processor.

7. The hearing prosthesis of claim 6, wherein:
the first housing is configured such that when the second housing is removably connected to the first housing, a body of the first housing is in direct contact with a body of the second housing.

8. The hearing prosthesis of claim 6, wherein:
the first housing and the second housing are configured to be removably connected to one another such that at least one of (i) the first housing supports the second housing when removably connected to the first housing or (ii) visa-versa.

9. The hearing prosthesis of claim 6, wherein:
the first housing and the second housing are configured to be removably connected to one another such that when the first housing is removably connected to the second housing, the second housing is spatially fixed relative to the first housing in three axes of the Cartesian coordinate system relative to the first housing.

10. The hearing prosthesis of claim 6, wherein:
the first housing and the second housing are respectively configured to be removably structurally supportably connected.

11. The hearing prosthesis of claim 6, wherein:
the first housing is configured such that when the second housing is connected to the first housing, no other housing is connectable to the first housing.

12. The hearing prosthesis of claim 6, wherein:
the first housing and the second housing collectively form part of a BTE device, wherein the first housing is configured to be placed behind an upper portion of the auricle and the second housing is directly connected to the first housing and configured to be located directly below the first housing when the first housing is located behind the upper portion of the auricle.

13. The hearing prosthesis of claim 6, wherein:
the second housing is a non-remote housing from the first housing relative to the second housing.

14. The hearing prosthesis of claim 6, further comprising:
a remote third housing.

15. The hearing prosthesis of claim 6, wherein:
a first electronic component is located in the first housing and a second electronic component is located in the second housing, wherein the first electronic component is signally connected to the second electronic component.

16. The hearing prosthesis of claim 6, wherein:
the first housing is part of a first module of the hearing prosthesis and the second housing is part of a second module of the hearing prosthesis, wherein the second module is both (i) removably connected to the first module via the removable connectable feature of the second housing and (ii) in signal communication with the first module.

17. The hearing prosthesis of claim 6, further comprising:
a remote module including a user interface configured to provide control of one or more features of the operation of the primary signal processor.

18. A method, comprising:
obtaining a BTE device including a first module including a first housing configured to be placed behind an upper portion of the auricle and a second module including a second housing directly connected to the first housing and configured to be located directly below the first housing when directly connected to the first housing when the first housing is located behind the upper portion of the auricle;
removing the second module from the first module and replacing the second module with a third module including a third housing such that the third housing is directly connected to the first housing, wherein the third housing is configured to be located directly below the first housing when the first housing is located behind the upper portion of the auricle.

19. The method of claim 18, wherein:
the second module is of a different configuration than the third module.

20. The method of claim 18, wherein:
the second housing is of a different configuration than the first housing.

21. The method of claim 18, wherein:
the second module has a different operational functionality than the third module.

22. The method of claim 18, further comprising the action of:
removing at least one of the second module or the third module from the first module and replacing the respective removed module with a fourth module including a fourth housing such that the fourth housing is directly connected to the first housing, wherein the fourth housing is configured to be placed directly below the first housing when the first housing is located behind the upper portion of the auricle.

23. The method of claim 18, wherein:
the second module has a different operational functionality than that of the third module and the fourth module; and
the third module has a different optional functionality than that of the fourth module.

24. The method of claim 18, wherein:
the method is executed by the recipient of the BTE device.

* * * * *